United States Patent
Bitoun (10) Patent No.: US 9,842,374 B2
(45) Date of Patent: Dec. 12, 2017

(54) PHYSIOLOGICAL INDICATOR MONITORING FOR IDENTIFYING STRESS TRIGGERS AND CERTAIN HEALTH PROBLEMS

(71) Applicant: Marc Jim Bitoun, Santa Cruz, CA (US)

(72) Inventor: Marc Jim Bitoun, Santa Cruz, CA (US)

( * ) Notice: Subject to any disclaimer, the term of this patent is extended or adjusted under 35 U.S.C. 154(b) by 485 days.

(21) Appl. No.: 14/217,158

(22) Filed: Mar. 17, 2014

(65) Prior Publication Data

US 2014/0329214 A1  Nov. 6, 2014

Related U.S. Application Data

(60) Provisional application No. 61/818,842, filed on May 2, 2013, provisional application No. 61/786,645, filed on Mar. 16, 2013.

(51) Int. Cl.

| G09B 23/28 | (2006.01) |
|---|---|
| G06Q 50/22 | (2012.01) |
| A61B 5/0205 | (2006.01) |
| G06Q 30/02 | (2012.01) |
| G06F 19/00 | (2011.01) |
| A61B 5/021 | (2006.01) |
| A61B 5/024 | (2006.01) |
| A61B 5/053 | (2006.01) |
| A61B 5/1455 | (2006.01) |
| A61B 5/11 | (2006.01) |

(52) U.S. Cl.
CPC ........... *G06Q 50/22* (2013.01); *A61B 5/0205* (2013.01); *A61B 5/02055* (2013.01); *G06F 19/3406* (2013.01); *G06F 19/3481* (2013.01); *G06Q 30/0269* (2013.01); *G09B 23/28* (2013.01); *A61B 5/021* (2013.01); *A61B 5/024* (2013.01); *A61B 5/0531* (2013.01); *A61B 5/1118* (2013.01); *A61B 5/14551* (2013.01)

(58) Field of Classification Search
CPC ........ G09B 5/08; G09B 23/28; G09B 23/281; G09B 23/283; G09B 23/285; G09B 23/286; G09B 23/288; A61B 5/02055; A61B 5/0205; A61B 5/021; A61B 5/16; A61B 5/165; A61B 5/167; G06Q 30/0269; G06Q 50/22
USPC .......................................................... 434/262
See application file for complete search history.

(56) References Cited

U.S. PATENT DOCUMENTS

| 2002/0019586 A1* | 2/2002 | Teller | A61B 5/02055 600/300 |
|---|---|---|---|
| 2005/0108049 A1* | 5/2005 | Ram | G06F 19/322 705/2 |
| 2010/0079508 A1* | 4/2010 | Hodge | G06F 3/013 345/697 |

* cited by examiner

*Primary Examiner* — Robert J Utama
(74) *Attorney, Agent, or Firm* — Eric P. Mirabel (57) ABSTRACT

Disclosed is a portable, wearable device for measuring parameters including blood oxygenation, galvanic skin response, skin temperature, pulse rate, blood pressure, and exertion level, and diagnosing stress and other conditions which cause stress-like physiological responses based on the results of the monitoring and on patient input of feelings and symptoms. Specific queries and advice on stress reduction, related disease management, and stress and disease education is also provided to the patient through the device.

15 Claims, 1 Drawing Sheet

PHYSIOLOGICAL INDICATOR MONITORING FOR IDENTIFYING STRESS TRIGGERS AND CERTAIN HEALTH PROBLEMS

BACKGROUND

The natural responses to stimuli in the environment, particularly stressors, trigger hormonal and physiological changes that activate the sympathetic nervous system and therefore disrupt homeostasis, the stable equilibrium conditions that regulate the body. The stress or fight-or-flight response is the part of the body's defense mechanism, and has as its purpose the redirecting of physical energy towards evading harmful or potentially deadly situations. In the process, hormones are released, notably cortisol and epinephrine, triggering various physiological changes that provide additional energy to the brain and muscles In the primitive environment most flight-or-fight responses were induced by life threatening situations, and were followed by intense physical activity, providing relief and the quick return to homeostasis. Modern day psychological or perceived stressors are much more frequent and most often are not followed by intense physical activity, leading to prolonged exposure to an activated sympathetic nervous system and stress-related hormones, including cortisol and epinephrine. While much research remains to be conducted on the matter, such chronic exposure to stress responses seems to suppress the immune system, opening the living system to attacks from viruses, bacteria and tumors, and has also been associated with various other negative health effects and negative effects on bodily functions, including:

- vulnerability to common infectious diseases such as colds and flu;
- digestive problems such as irritable bowel syndrome and ulcers;
- increased vulnerability to anxiety and depression;
- cortisol contributes to infertility and increased risks of miscarriage;
- premature aging;
- slow wound healing;
- impairment of developmental growth in children;
- cortisol has been linked to impairment of learning and memory loss; and
- accumulation of visceral fat, which is itself linked higher risks of heart attack and stroke.

With so many adverse health effects linked to stress, there is a need to properly diagnose or bring awareness to situations which cause stress or disrupt homeostasis, so that they can be better avoided or so that stress coping mechanisms, such as physical activity, thinking pleasant thoughts or listening to music, can be deployed. There is also a need to record the events causing stress and the stress responses associated with them so that events causing stress, and which events caused more significant amounts of stress, can be determined, so as to aid in avoidance or treatment subsequently.

Any means for diagnosing stress responses should be light and easily portable, so that the user can use it ubiquitously, and in the user's normal environment—rather than only in a medical setting.

SUMMARY

A device for diagnosing stress and other conditions which cause stress-like physiological responses has its components preferably contained in a wristband, to be worn by the user. The device can capture physiological information that is processed, then recorded, for later access, and/or displayed immediately. The information can also be wirelessly transmitted to a user's cell phone, computer or anywhere else for storage or analysis, or transferred from a port on the device to a flash drive or other storage medium.

The device also preferably accepts user input, including, patient feelings, specific symptoms, frequency of symptoms, clinical history, and responses to specific inquiries relating to stress stimuli or disease indicators. This input is used in performing the diagnosis and recommending corrective actions or treatment. The device can also provide the patient (through the display or otherwise) advice on treatment and education for stress and stress avoidance, and treatment and education about diseases and conditions the device can help detect or treat.

The recorded information can be summarized and displayed for the user, and the user's outcomes and symptoms can be tracked, in order to encourage continuing user compliance with stress-relief protocols and use of the device. That is, if the user's symptoms improve, or the user's disease outcomes improve as a result of using the device, this information can be tracked over time and displayed for the user. Another related use of the data is to determine if multiple users' symptoms improve, or their disease outcomes improve as a result of using the device, and then that information is used in advertising the device and its benefits to promote these benefits to a larger audience. Such promotion would help recruit new patients to use the system, and thereby improve the outcomes and reduce stress and overall health of an increasing proportion of the patient population.

DETAILED DESCRIPTION

Among the stress-related physiological indicators which are monitored by the device are:
- galvanic skin response;
- skin temperature;
- heart/pulse rate;
- blood oximetry;
- blood pressure; and
- breathing rate or pattern.

The wristband with the active components should provide an unobtrusive, lightweight and comfortable fit for the user. Preferably, the display is only viewable on activation by the user so that unintended viewers cannot observe the user's stress levels. Limiting the view of the display can also be accomplished by having it face inside on the wristband. The data can be viewed in real time or logged and viewed later based on any of: time of day sampled, following meals or activities, as averages over time, highs, lows, as graphic displays, or otherwise as selected by the user.

In addition, device could include a pedometer or accelerometer to monitor steps or user exertion levels, and calories expended. The pedometer or accelerometer can also serve as a control indicator, to differentiate stress episodes from normal physical activity (especially where there is remote monitoring), as stress can cause similar physiological responses to exertion. The effect of various levels of exertion on the physiological indicators above could indicate which exercise or exertion level is more desirable or effective, which help in treatment, or which are unsafe.

Ambient temperature and humidity may also be monitored and analyzed with other input in the device. Again, changes in these environmental factors can cause similar physiological responses to exertion or stress.

In addition to providing a user-friendly record and display of stress indicators, the device and system described are also useful in diagnosing several diseases and conditions that affect one or more of the physiological indicators monitored by the device; e.g., cardiovascular diseases including hypertension, arrhythmia, heart murmurs and atrial or ventricular fibrillation. The disease progress, patient therapy and drug use, symptoms and long term outcomes (i.e., increased or decreased serious cardiovascular problems or death) can be monitored and recorded, to encourage the patient's compliance or to recruit more patients (through advertising).

The wireless feature allows monitoring of users remotely, which could be useful for monitoring for heart problems or breathing problems, e.g., in a health care setting, or where patients are monitored at home or remotely. The wireless feature with the physiological indicators also permits sleep monitoring, determining quality and quantity of sleep and diagnosis of sleep apnea. In all such cases where a problem is detected, the device could have an alarm feature which would be activated to alert the user or a health care worker to take appropriate action, including CPR or other emergency action in the case of acute heart problems.

Similarly, the user could be alerted to high stress and could be instructed to take medication to alleviate the symptoms, such as benzodiazapenes, sleep aids (Ambion), anti-anxiety medication, SSRIs or medical marijuana. Use of such medications is a negative outcome and eliminating or reducing medication use is a positive outcome goal provided by using the system. Similarly, decreased occurrence of diseases and conditions associated with stress can be tracked and recorded, and alleviating or ameliorating symptoms by use of the system, or improving disease outcomes, or lessening predicted incidence of sequalea or disease progression, is considered as positive outcomes (which can be used as noted above for compliance or promotion).

Also included is a business based on periodic charges to users for a monitoring service for device users. The monitoring in this case could be remote or could be of patients in a health care setting. The monitoring could also include recording stress indicator responses, and alerting a health care provider in the event of highly irregular or contraindicated responses. Such recording through a monitoring service is another means of correlating a record of system use and stress-relief protocols with symptoms and/or outcomes—where the system includes publicizing improvements in outcomes and symptoms.

The sections below describe the device operation and how it monitors ambient and physiological indicators that may be useful in diagnosing clinically relevant episodes of stress, or indicating the user's physiological state, disease or condition. Table I below shows: for a number of parameters monitored, considerations relating to the monitoring of the parameter and making of diagnosis based on it; immediate questions to the user and input of responses where certain parameter limits are reached; and, based on the parameter and the responses: additional questions and advice to the user. The questions and advice can be projected directly on the device display, or sent wirelessly to the user's PDA, cellphone or computer. The user input can also be directly into the device, or can be sent to the device wirelessly after input through the user's PDA, cellphone or computer.

TABLE I

| Medical Decision Tree: | Algorithm differentiates sleep from wakefulness; or, user inputs when he/she goes to sleep and wakes either through the device or via a mobile interface. Oximetry is the primary parameter in diagnosis of stress; GSR (galvanic skin response) and skin temp. and other parameters below can differentiate stress response from other arousal responses |

| | | Medical | | | Analysis Check and Ask - | Feedback Long Term Feedback - |
|---|---|---|---|---|---|---|
| Parameter | Sample Rate: | Characterize | Value | Diagnosis | Instant Feedback | Medical Suggestion |
| Pulse | Number of beats per unit of time, e.g., 10 seconds | Regular | value < 60 | Healthy: Athlete Panic Attack If perceive/feel palpitation then determine if stress-related | CHECK: GSR - Skin Temp ASK: History of cardiovascular Problems? 1. Athlete: No problem 2. Panic Attack: Advise - take action 3. Palpitation: Ask if stress, if so: | EKG/ECG chest strap could help sharpen diagnosis. If Athlete, then no feedback necessary; Positive Feedback is optional If not an athlete then could be a panic attack - |

TABLE I-continued

| | | | Suggest => coping mechanism;/ BUT IF; it persists, Check Frequency: | Send "snap out of it" comment and suggest relaxation If Palpitations are felt and this is due to a stressful event then suggest establishing a coping mechanism If Palpitations occur frequently then advise getting help from a Dr. - Self evaluate lifestyle and eliminate as much as possible events that cause this reaction |
| | 60 < value < 100 | Healthy | No questions | Give Positive Feedback |
| | value > 100 | if Healthy: could be caused by arousal or panic attack; or, caused by cardiovascular Problems | Check also: Motion, Skin Temp, GSR ASK: Feel OK? ASK: Arousal/ Palpitations/ Stress/ Panic Attack? IF: 1. Arousal: Positive Feedback, or, IF 2. Stress/ Panic Attack/ Palpitations/ Feel Bad: ASK: Happen Often? | EKG/ECG chest strap could held sharpen diagnosis If feel Ok then give positive feedback: this is positive arousal If user feels bad or palpitations are felt then classify as panic attack/ stressful event - Suggest coping by exercise and relation If occurs frequently then advise getting help from a Dr. - Self evaluate lifestyle and eliminate as much as possible events that cause this reaction |
| Irregular* | value < 60 | Caused by: Bradycardia; Cardiorespiratory Problems; - stressful event; or Other | ASK: Feel OK? | Feedback: if stressful event detected If occurs frequently then advise getting help from a Dr. - Self evaluate lifestyle and eliminate as |

TABLE I-continued

| | | | | | | |
|---|---|---|---|---|---|---|
| | | | 60 < value < 100 | shortness of breath Panic Attack | Check: Motion, Skin Temp, GSR ASK: Feel OK? Frequency? | much as possible events that cause this reaction Snap Out of stress state - Find stressors and Avoid; Suggest Exercise - Relaxation - Medical Advice; Talk to someone to reduce stress; EKG/ECG chest strap could held sharpen diagnosis |
| | | | value > 100 | Tachycardia Cardiorespiratory Problems Panic Attack | Check: Motion, Skin Temp, GSR ASK: Feel OK? Frequency? | If Panic Attack: Snap Out of stress state - Find stressors and Avoid; Suggest Exercise - Relaxation - Medical Advice; Talk to someone to reduce stress; EKG/ECG chest strap could held sharpen diagnosis |
| Oximetry | Monitored at regular intervals; e.g., Every 10 seconds | Value | <73 | Night time: Apnea/ Hypopnea | Check: Motion, Skin Temp, GSR ASK: Feel OK? Frequency? | See Doctor: Blood Test, Cardiovascular and Cardiorespiratory Exams; sleep apnea is highly possible (extreme episode of apnea); Suggest Medical Advice |
| | | | | Daytime asthma/ dyspnea Chronic Bronchitis (with additional questions) Pulmonary Embolism Cardiac Ischemia | Check: Motion, Skin Temp, GSR ASK: Feel OK? Frequency? | |
| Oximetry | Monitored at regular intervals; e.g., Every 10 seconds | Value - Number of Events of apnea/hypopnea per unit time | 73 > x > 93 | Night time: Apnea/ Hypopnea | Check: Motion- Irregular heart- or Increasing Heart Beat ASK: Tired during the day? - Feel Fatigues? Fall Asleep Easily? Fall asleep immediately? | Advise: Don't drive - See a doctor If Fatigue felt often and fall asleep fast and easily then diagnosis is sleep apnea: Advise on Long Term issues, e.g.: Obesity, Cardiovascular Problems, Death - Talk to a physician |
| | | | | Daytime asthma/ dyspnea Chronic Bronchitis | Check: Motion, Skin Temp, GSR ASK: Feel | Advise: Don't drive; See a doctor Advise on Long Term |

TABLE I-continued

| | | | | | | |
|---|---|---|---|---|---|---|
| | | | (with additional questions) | OK? Smoke? Asthma? Emphysema? Shortness of Breath? | issues, e.g.: Obesity, Cardiovascular Problems, Death Areas to investigate for causation: Anemia panic attack hyperpnea and panic attack bradycardia/ tachycardia; Suggest Medical Advice | |
| Oximetry | Monitored at regular intervals; e.g., Every 10 seconds | Value | >93 | Healthy Breathing | N/A | Breathing Well |
| Motion | Monitored at regular intervals; e.g., Every 10 seconds | Value | | Motion detection equates with activity levels | | |
| GSR or Skin Conductivity | Monitored at regular intervals; e.g., Every 10 seconds | Value | value: change relative to patient baseline | Determine activity and stress relief | | |
| Pulse and Oximetry determined at a frequency greater than once per second | Difference between inhale and exhale (pulse normally slows on exhale) | Pulse on exhale slower than on inhale | N/A | Normal/ Healthy | | Combined with Oximetry in diagnosis and recommendations |
| | | Pulse on Exhale = Inhale | | Heart Problems Hyperadrenaline Stress or related to stress | | Combined with Oximetry in diagnosis and recommendations |
| | | Pulse on Inhale slower than exhale | | Heart Problems Hyperadrenaline Stress or related to stress | | Combined with Oximetry in diagnosis and recommendations |
| Blood Pressure | Constant: record only episodes of highs/ lows or irregularity, or average per hour Amplitude | Amplitude Max | | Systolic Hypertension | | Measure at Rest to Verify Diagnosis |

Figure 1:
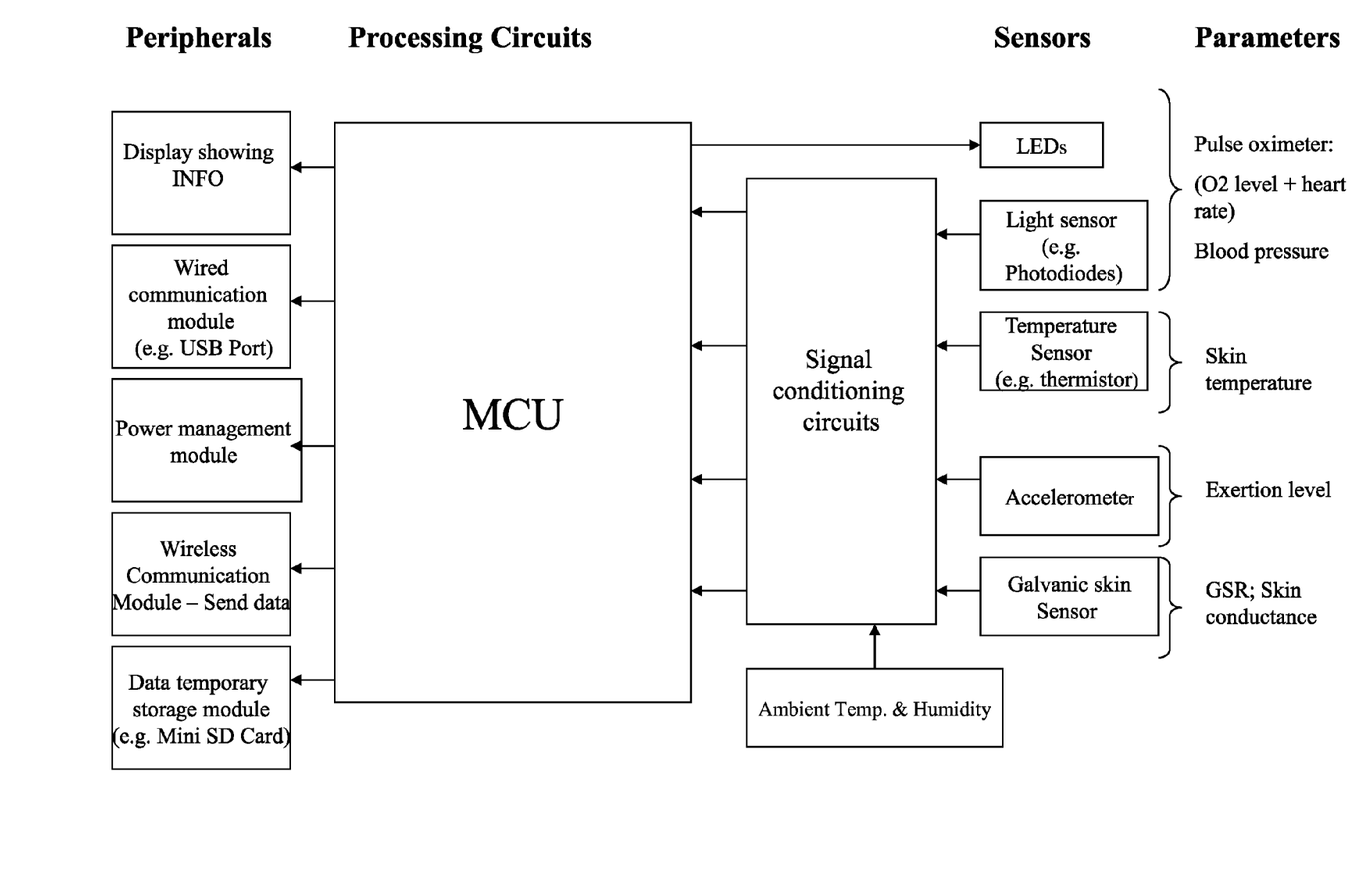
FIG. 1 is a flow diagram showing: the parameters measured (far right column), sensors for measuring the parameters (next to far right column), signal conditioning circuits for: conversion of the signals to digital and for signal amplification. A microprocessor (MCU) is for code execution from the sensors to perform the diagnostic functions. The output from the microprocessor is then sent for storage in, e.g., a mini SD card or transmitted for storage to another device (using e.g., a USB port and USB drive) or to a wireless communication module. The output is also sent for display to the user, preferably upon activation of the display function by the user but not otherwise. The output is also passed to the power management module, to be used to regulate use of the batteries (which are preferably re-chargeable).

Referring to FIG. 1, the Microcontroller (MCU) is the processing unit for all data collected and output. It can preferably be designed using an 8-bit microcontroller (MCU) (Freescale P/N MC9S08MM128) with built-in peripheral features such as serial peripheral interface (SPI), Inter-intergraded circuit (I2C), Analog-to-Digital Converter (ADC), USB on-chip transceiver, operational amplifiers (OPAMP) and trans-impedance amplifiers (TRIAMP). The MCU should preferably have at least 128 KB of on-chip flash memory where the firmware is stored to run the algorithms that capture, store, and analyze the multiple biological and environmental signals from the sensing units. The MCU should also have enough pins to accept and output all the required circuits.

To reduce the cross-talk and noise from the MCU to the other modules, the power supply lines are preferably separated into three types: MCU3.3V (for MCU only), VDDA (for analog circuits), and +3.3V (for digital circuits). These circuits are preferably decoupled with decouplers composed of capacitors and inductors, that reduce the noise to the power supply lines.

Two or more external oscillators are used to provide the clock signals to the MCU. The MCU also preferably has a built-in background debugging feature which can be used for debugging purposes and to load firmware into its memory. A "reset" button S1 should also be included to provide the system-level reset.

The specific operation of the sensors shown in FIG. 1 are set forth below.

Blood Oxygenation and Pulse Rate

As noted, blood oxygenation is a primary indicator of health and stress levels, as stress induces increased breathing rate which increases blood oxygenation.

The pulse rate (heart rate) varies with the body's need to absorb oxygen and excrete carbon dioxide, and there are wide variations between the rate when exercising, sleeping, and other physiological states. Pulse rate assists in the diagnosis and tracking of medical conditions and physiological states, including stress level, as it increases adrenaline (epinephrine) and cortisol in the system, which in turn elevates the pulse rate.

A pulse and oximetry combined module (see FIG. 1) can be used to measure the oxygen saturation level in blood as well as the heart rate (pulse rate) of the user. Oximetry relies on shining light through blood vessels on the skin, e.g., finger tip or earlobe, where the amount of light absorbed or reflected is related to the oxygen concentration in the blood. Pulse rate can be derived by determining the characteristic of the oxygenation level variance over each heartbeat. Alternatively, pulse rate could also be measured by other commercially available sensors, such as a chest strap (see table I).

For oximetry, light of two different wavelengths (red and Infrared, of about ~660 nm and ~880 or 940 nm, respectively) is preferred. The light is emitted by two or more different light-emitting diodes (LEDs) (e.g., those made by Measurement Specialties of Hampton, Va.; the P/N ELM-4001 or ELM-4002). These wavelengths are preferred because deoxygenated blood has higher absorption at 660 nm and oxygenated blood has higher absorption at 880 or 940 nm. A photodiode or sensor (Measurement Specialties' P/N EPM-4001 or EPM-4002) which is specifically designed to capture these wavelengths is used to detect the amount of light that transmits/reflects through or from the skin. The light will generate an electrical current on the photodiode, which will then be converted to a voltage, which is filtered and amplified and sent to the MCU for storage and analysis.

The first stage of an exemplary signal conditioning circuit for a pulse oximetry module has a lowpass filter, composed of a TRIAMP circuit which converts the current from the photodiode sensor to a filtered voltage output. The TRIAMP can be built into the MCU (U1) or formed with external amplifiers. The photodiode sensor anode and cathode can be connected to the TRIAMP. The lowpass filter can have a cutoff frequency ($f_c$) at 125 Hz (i.e. $1/(2*\pi*4.7\ M\Omega*270\ pF)$). A small offset voltage of roughly 0.3 to 0.4V (i.e. $1.2\ K\Omega/11.2\ K\Omega*3.3V$) can be set at the input to offset/bias the negative part of the AC signals, and the gain of the stage can be set to $4.7 \times 10^6$ by the resistor R13. A large resistor of M$\Omega$ range (i.e., $4.7\ M\Omega = 4.7 \times 10^6 \Omega$) is used because the current generated from the photodiode is small—in the microampere ($\mu A$) range (i.e. $10^{-6}$ A). Using a large resistor will provide sufficient gain to convert the voltage into a measurable range.

A second stage of the signal conditioning circuit for the pulse oximetry module, with a filtering and amplifying circuit for the red related signals, is preferred. First, the raw voltage output from the TRIAMP circuit is sent through a lowpass filter composed of R1 and C4 with cutoff frequency $f_c$ of 6 Hz (i.e. $1/(2*\pi*2.7\ K\Omega*10\ \mu F)$). This first filtered signal will be sent to an Analog-to-Digital Converter (ADC) of the MCU to adjust the intensity of the Red LED.

The $2^{nd}$ filter stage is a 60-Hz notch filter composed of R2, R3, R4, C5, C6, and C7 (with $f_0=60\ Hz=1/(2*\pi*27\ k\Omega*0.1\ \mu F$ since $R=R3=2*R4=27\ K\Omega$ and $C5=C6=C7/2=0.1\ \mu F$).

The 3rd filter stage is a highpass filter composed of C8 and R6 with $f_c=0.8\ Hz\ (1/(2*\pi*56\ K\Omega*3.3\ \mu F)$.

The 4th filter stage is an active lowpass filter composed of R7, R32, C9 and the OPAMP from the MCU. Its cutoff frequency is 6 Hz ($f_c=6\ Hz\ (1/(2*\pi*4.7\ M\Omega*5600\ pF))$ with gain of 31 ($-4.7\ M\Omega/150\ k\Omega=-31$).

The 5th filter stage is again a lowpass filer composed of R8 and C10 with $f_c=4.8\ Hz\ (1/(2*\pi*3.3\ K\Omega*10\ \mu F)$. The final output will be sent to the MCU.

For the infrared related signals, the same signal conditioning circuits as for the red signals are preferably used. The final output is also sent to the MCU.

In the absence of a negative power supply, one needs to create a reference bias voltage that can offset any negative component of the AC signal, which can be done, for example, using a VCC/2 reference signal generator. The circuit can be made using the built-in TRIAMP circuit in the MCU to make a voltage follower circuit. Again, no external amplifier is required. Resistors are used to set a 50% ratio voltage divider to feed the VCC/2 reference signal to a non-inverting input of the TRIAMP. Then, an inverting input of the MCU can be tied to an output to form the voltage follower circuit. The VCC/2 reference voltage is also fed to different pins of the MCU for offset/biasing any negative part of the AC signals in the subsequent conditioning circuits.

To keep the system simple, it is preferred that a single photodiode is used to detect both the red and infrared signals. To separate the signals related to these wavelengths, the red and the infrared LED are switched ON alternately. A driving circuit is needed to provide sufficient current for the LED. The LED is placed (e.g. on the wrist) to emit light to the user's blood vessels. The actuation timing and the light intensity of the LEDs are controlled by signals from the MCU unit.

To separate the signals related to the two different wavelengths (i.e., red and infrared), a multiplexer circuit is preferred, such as a 4 channel 4×2:1 switch U1 (e.g., Fairchild Semi P/N FSAV430QSCX). The output of each channel will be dependent on a switch control signal, such that either the Red or the Infrared related signals are sent to the MCU at any given time.

Blood Pressure

Blood pressure usually refers to arterial pressure of the systemic circulation. Blood pressure is the result of the pumping of blood by the heart against the resistance to flow through the blood vessels. Stress influences blood pressure. However, as many other factors also affect blood pressure, it alone cannot accurately measure stress, but with consideration of other indicators, can be a useful co-indicator.

Devices such as the sphygmomanometer are typically used to measure blood pressure, by restricting blood flow with an inflatable cuff, and a mechanism to measure pressure. The exerted obstructing pressure may be used to determine the internal blood pressure in the body. Other devices and measurements may be used to infer blood pressure, or collect relative blood pressure measurements such as collecting and quantifying the sound of the heart, or the electrical response of the skin to the heart beat.

Other devices to measure blood pressure include Photo Optic sensors such as the oximeter described above. The delay in signal between two locations in blood flow can be used to infer the blood pressure, as determined by the light emitted and detected by the oximeter. Piezo sensors can also measure such delay and thereby infer blood pressure, as can electret microphones. All these devices are readily available commercially.

Galvanic Skin Response

The galvanic skin response (GSR) results from fluctuation of the skin electrical conductance due to varying moisture levels. As sweat gland output is controlled by the sympathetic nervous system, skin conductance provides an indicator of psychological or physiological arousal. The Galvanic Skin Repose is widely recognized as an indicator of emotional and physiological arousal, physiology and psychophysiology. For example, the polygraph test measures it along with other parameters to detect deception.

Skin conductance is the inverse of electrical resistance and can therefore be using a system like an Ohmmeter, e.g., two electrodes in contact with the skin as part of a properly calibrated system, to detect differences in skin conductance, in the order of micro Siemens, associated with sympathetic activity, and therefore arousal level.

Skin conductance alone may not be used identify the type of arousal an individual is subjected to, as fear, anger, startled response, orienting response and sexual feelings may also produce sympathetic activity and similar skin conductance responses. Accordingly, other parameters and patient responses need to be considered.

Referring to FIG. 1, the Galvanic skin response (GSR) module is used to measure the skin conductivity or the so-called electrodermal activity (EDA). To achieve that, a small 0.5V reference voltage can first be sent to the user's skin through an electrode which is connected to an amplifier. Another electrode connected to another pin of the amplifier is used as the return path for that 0.5V signal. As the skin conductivity (or resistance) is changed, the current that passes through the skin will change, resulting in a changed voltage at the amplifier. This small raw voltage is then preferably passed through 4 stages of active filtering and amplifying before it is sent to the MCU.

To cover a wide range of skin conductivity, the first amplifier's gain is automatically selected from one of four possible gains (i e using 4 different resistors), where the selection is controlled by the MCU, to prevent signal saturation. The gain selected will be based on the feedback baseline signal fed to the MCU after the $2^{nd}$ amplifier stage. The details of these circuits are described below.

The circuit that is used to produce the 0.5V reference signal can be composed of U3 (Linear Technology P/N LT1635CS8 #PBF), which is an OPAMP with a built-in precision reference voltage of 0.2V. Using that reference 0.2V, an OPAMP circuit can be used to generate a gain of ~2.5 (i.e. A=1+R40/R39=2.5=A=1+3 KΩ/2 KΩ=2.5) and the reference output of +0.5V. Per the data sheet of U3, a capacitor circuit is added in case there is a capacitive load at the output.

The 0.5-V reference voltage that is applied on the skin will first generate a current which returns via an electrode. This current then flows through a resistor and generates a voltage at the input of an OPAMP with a gain which is adjustable by changing the resistance across the OPAMP. This resistance will be automatically chosen by the MCU from one of the 4 resistors connected through a switch based on the feedback voltage from $2^{nd}$ amplifier stage. The output of the OPAMP stage will be an amplified version of the voltage input which will be sent to the next stage for more signal conditioning.

The second stage of the signal conditioning circuit can be a 2nd order Sallen-Key lowpass filter with a gain of 2 and a cutoff frequency $f_c$ of 5 Hz. The output from the $1^{st}$ stage will be filtered for high frequency noise and amplified before sending to the next stage. To achieve that, the filter is preferably composed of one of the OPAMPs from U5 (Texas Instruments P/N LMP2014MT) with R42, R46, R47, R49, C47, and C37. The gain is calculated as A=1+R42/R49=1+10 KΩ/10 KΩ=2 whereas the cutoff frequency ($f_c$) is calculated as $\frac{1}{2} \times \pi * (R46*R47*C37*C38)^2 = 1/(2*\pi*470\Omega \times 1 K\Omega \times 47 \mu F \times 47 \mu F) = 5$ Hz.

The output of this stage is the low frequency (f~0 to 0.05 Hz) baseline component, or the so-called tonic component of the galvanic skin response. This baseline component serves two purposes. First, it is used as the feedback signal to the MCU such that it can choose the right resistor (i.e. the right gain) in the $1^{st}$ stage to prevent signal saturation. The second purpose is to provide the baseline signal for the subsequent stages for further filtering and amplification.

The output from the 2nd stage is filtered and amplified again in this third stage (and in the next stage) to extract the phasic component (f~0.05 to 2 Hz) of the galvanic skin response. This can be done using a $2^{nd}$ order Sallen-Key highpass filter with a gain of 2 and a cutoff frequency $f_c$ of 0.05 Hz. The filter is composed of one of the OPAMPs from U5 (Texas Instruments P/N LMP2014MT) with R43, R51, R52, R55, C34, and C35. The gain is calculated as A=1+R43/R52=2 whereas $f_c$ is calculated as $1/(2\pi*(R51*R55*C34*C35)^2)=0.05$ Hz. The output will be sent to the last stage for more signal conditioning before sending to the MCU.

The output from the $3^{rd}$ stage is filtered and amplified again to extract the phasic component (f~0.05 to 2 Hz) of the galvanic skin response. This stage is a $2^{nd}$ order Sallen-Key lowpass filter with a gain of 2 and a cutoff frequency $f_c$ of 5 Hz. The filter is composed of one of the OPAMPs from U5 (Texas Instruments P/N LMP2014MT) with R41, R44, R45, R50, C36, and C39. The gain is calculated as A=1+R41/R50=2 whereas $f_c$ is calculated as $\frac{1}{2}\pi*(R44*R45*C36*C39)^2=5$ Hz. The output of this stage is the fast changing (f~0.05 to 2 Hz) component of the galvanic skin response and is designated as Phasic EDA. The output is sent to the MCU for analysis Skin Temperature Certain emotional and psychological states can cause measurable changes in skin temperature as they can activate the sympathetic nervous system, which leads to a reduction of the peripheral circulation. Skin temperature may therefore be used as an indicator of psychological or physiological arousal.

Measuring skin temperature alone usually does not provide enough information to determine the arousal state of an individual as it also depends on, for example, the external temperature and humidity, the air circulation, the user's genetics and health. It is useful in combination with other indicators, especially if external temperature, humidity and/or air circulation are factored into the determination.

Various method may be used to measure the typical skin temperature variations of 1 to 2° F. resulting from arousal, in a controlled or held constant environment or where the ambient temperature varies widely. Referring to FIG. 1, commonly used devices for skin temperature measurements include a thermocouple, a thermistor (made by, e.g., Measurement Specialties) and the Resistance Temperature Detector. An RTD temperature probe (available from Digikey Corp.) can also be used to measure skin temperature, though it does not have the sensitivity of a thermistor.

One example of a suitable thermistor module is to use a negative temperature coefficient (NTC) thermistor (e.g. Cantherm P/N MF52C1503F3950), which is placed on the patient's skin. The leads of the thermistor are connected to a module where a voltage divider is formed. Any increase in the skin temperature will result in a reduction of its resistance and an increase in the voltage at one pin of the voltage divider. This voltage is the raw input related to the skin temperature and is sent to the MCU, after filtering and amplifying.

First, to reduce the high frequency noise, a lowpass filter composed can be connected after the raw voltage signal at the voltage divider. The cutoff frequency is $f_c=1.6$ Hz $(1/(2*\pi*100\ K\Omega*1\ \mu F))$. The filtered signal is then fed to an OPAMP circuit composed of U2 (Texas Instrument P/N OPA333AID), R30 and R31 with gain of ~3 (i.e. $A=1+20\ K\Omega/10\ K\Omega=3$). The output is then filtered and amplified, and the signal is then sent to the MCU.

Ambient Temperature and Humidity

Ambient temperature may be measured using the same sensors as for measuring skin temperature. Ambient humidity may be measured by various means, including hygrometers and psychrometers. Hygrometers measure changes in shape of conductivity of a material based on its absorption of moisture from its surroundings. The psychrometer use wet and dry bulb temperature measurements to infer humidity levels. Ambient temperature and humidity measurement can be obtained through a sensor IC, such as the P/N Si7020-A10-GM made by Silicon Labs, Austin, Tex. The results are sent at pre-set intervals to the MCU using an interface.

Physical Motion (Exertion)

Physical exertion causing motion, affects the physiological indicators above. Physical motion may be detected and measured using common technology currently used in pedometers and other commercial step indicators, including accelerometers, see, e.g., U.S. Pat. No. 8,066,640 (incorporated by reference), or another 3-axis digital accelerometer (Freescale Semiconductor, Austin Tex. P/N MMA8652FCR1). To save power, the active mode of the accelerometer can be switched between the sleep and the wake mode using the interrupt input. The data related to the acceleration/motion of the 3 axis are sent to the MCU via an interface with a clock and data line.

Peripheral Unit—USB Charging and Battery Monitoring Module

The power for the device is preferably provided by a rechargeable Li-Ion/Polymer battery, which can be recharged using a micro USB port. Once connected to a USB power source, a +5V DC voltage is sent to the system as well as the VBUS line of the MCU. A transient voltage suppression (TVS) unit should be connected to all the relevant data and power lines in the USB connector.

During battery charging, the +5V DC voltage from the USB power source is preferably first sent to a Li-Ion/Polymer battery charger and power-path management IC (which is designated as U7 and made by Texas Instruments P/N BQ24075TRGTT). To keep the design simple, no external thermistor is used and a corresponding thermistor pin is directly connected to a 20% ratio voltage divider as suggested by the data sheet of U7 (Texas Instruments P/N BQ24075TRGTT). To set an input current limit of 1.5 A, an external resistor (designated as $R_{ILIM}$ or Maximum input current programming resistor) is connected to the adjustable current limit programming pin of U7. The details to calculate this resistance $R_{ILIM}$ is shown in details below:

$R_{ILIM}=K_{ILIM}/I_{IN(max)}=1600\ A\Omega/1.5\ A=1.07\ K\Omega$ where $K_{ILIM}$ is the Maximum input current factor given by the data sheet of U7 and $I_{IN(max)}$ is the maximum input current limit To enable the input current limit with the ILIM pin, EN2 and EN1 must be set to +5V (signal high) and GND (signal low). Similarly, to program the fast charge current level of 0.5 A at ISET of U7, an external resistor (designed as $R_{ISET}$ or Fast charge current programming resistor) is used. The details to calculate this resistancies given below:

$R_{iset}=K_{ISET}/I_{CHG}=890\ A\Omega/0.5\ A=1.78\ K\Omega$ where $K_{ISET}$ is the Fast charge current factor given by the data sheet of U7 and $I_{CHG}$ is the Battery fast charge current limit There are two outputs from U7. The first one is OUT, which is used to feed the voltage regulator U9 (Texas Instruments P/N LP2985A-33DBVR). This voltage regulator provides the main power supply of +3.3V for the other modules described above. The second output from U7 is connected to the anode of the Li Ion/Poly battery through power transistors, which are used to provide a system level power shutdown or power toggle with a switch. When it is not charging, the battery will feeds the output and the other modules.

To show the USB charging status, U7 also provides two signals to the MCU. The first one is is pulled to ground when a valid input source is detected. Otherwise, the first signal is high-impedance in cases of unacceptable input power. The second signal for monitoring of the charging status pulls to ground when the battery is charging. Otherwise, the second signal is high-impedance when charging is complete or when the charger is disabled.

To show the time it takes to charge the battery and the amount of energy left, a battery gauge IC (designated as U8 and made by Texas Instruments P/N BQ27200) and some associated components are used. To determine the charging and discharging activity of the battery, U8 basically monitors the voltage drop across a small current sense resistor that is connected in series with the battery cathode and the system ground.

Peripheral Unit—MicroSD Card Module

Since the on-chip memory of the MCU is limited, a microSD card can be inserted to provide additional memory. The communication between the microSD card module and the MCU is done via a serial peripheral interface (SPI1). In this case, a clock signal is provided and data lines are used to send data to/from the microSD card.

Peripheral Unit—LCD Display Module

The LCD display module communicates with the MCU via a $2^{nd}$ serial peripheral interface (SPI2). LCD module NOKIA3310 is selected due to its simplicity and its ready availability for development and debugging purposes. However, an OEM or custom LCD display may be used instead.

Wireless Communication Module

Data captured by the sensors are stored in the microSD card for further processing using the USB interface or an external microSD card reader. A wireless communication module composed of a wireless transceiver chip and an antenna can be included so that data can be transferred wirelessly to a mobile computing device (e.g. smart phone, tablets, or other) using existing protocols such as Bluetooth, GSM, and 802.11 (WiFi). Additional commands can also be sent to the device wirelessly from a monitoring station (below) based on feedback to the data received.

Transmittal to a Monitoring Station or to Others

All the parameters measured by the device and output can be transmitted to a central monitoring station. The station can process and analyze the information received further and provide real-time advice, education and even alerts to the user, in the even acute health problems indicate action is needed. The monitoring station can also provide any or all of the queries, advice, educational messages or stress relief protocols, as set forth in Table I. The station can also do the recording of data, symptoms and outcomes for the patient. This recorded information can be used to encourage patient compliance or as promotion to recruit more patients for the system.

All the output from the device can also be transmitted to others, as approved by the user, e.g., family members, healthcare providers, insurance companies, corporate entities, payers, research entities and partners.

The specific methods and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing, by Applicants. The invention has been described broadly and generically herein. Each of the narrower species and subgeneric groupings falling within the generic, disclosure also form part of the invention.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of reducing stress in a number of patients by monitoring stress indicators and providing information on stress reduction to patients, and then using lessened stress or improved clinical outcomes from these patients to recruit additional patients and apply the method to them, comprising:

providing patients with a device whose components are incorporated in a wrist-band to be worn by the patients, and which includes sensors for measuring the following parameters: skin temperature, galvanic skin response, blood pressure, pulse rate, blood oxygenation, ambient temperature, and exertion level; and wherein the device further includes a microcomputer and software combination embodied in a non-transitory computer readable medium which jointly perform the following steps (i) to (iii):

(i) analyzing and recording the parameters and displaying for the patient queries relating to diagnosis of stress or diseases or conditions;

(ii) providing advice to the patients on stress-relief, including one or more of: find stressors and avoid them; exercise; relax; and, talk to someone to reduce stress; and (iii) publicizing stress reduction or improved clinical outcomes in order to recruit new patients to use the method, based on a majority of the patients applying the advice in order to reduce stress or improve clinical outcomes.

2. The method of claim 1 wherein the parameters are transmitted to a central monitoring location which provides the queries and advice, and further provides education to the patient.

3. The method of claim 1 wherein the parameters are transmitted to the patient's cell phone or computer.

4. The method of claim 1 wherein the wrist-band includes a display which can be seen upon activation by the user.

5. The method of claim 1 wherein the recorded parameter can be displayed based on time recorded, or in connection with activities or events.

6. The method of claim 1 further including alerting the user in the event of a likely health problem.

7. The method of claim 6 further including advising the patient to consume medication.

8. The method of claim 1 wherein the recorded parameter can be tracked and displayed over time.

9. The method of claim 8 wherein the recorded parameter can be later displayed based on time of day sampled.

10. The method of claim 8 wherein the recorded parameter can be later displayed following meals or activities.

11. The method of claim 8 wherein the recorded parameter can be later displayed as averages over time.

12. The method of claim 11 wherein the recorded parameter displayed can also show high and low values of each parameter.

13. The method of claim 11 wherein the display is a graphic display.

14. The method of claim 1 wherein the device further includes a pedometer or accelerometer to monitor steps or user exertion levels, or calories expended.

15. The method of claim 1 wherein the device further includes means for monitoring ambient temperature or humidity.

* * * * *